Nov. 12, 1963 L. MORO Plant Pat. 2,301
ROSE PLANT
Filed Oct. 4, 1962
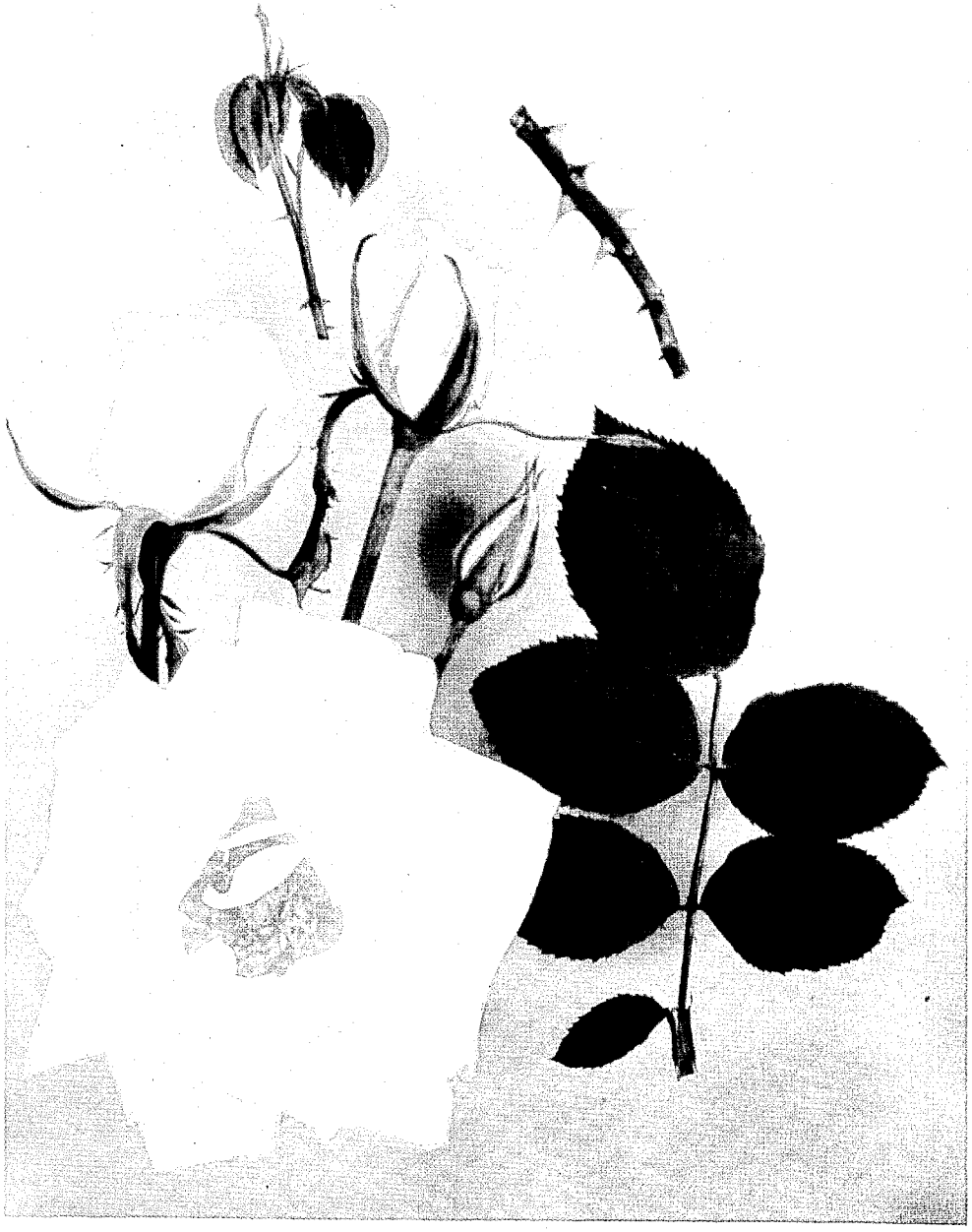
Inventor.
Luciano Moro
By: Robb & Robb
Attorneys.

United States Patent Office

Plant Pat. 2,301

Patented Nov. 12, 1963

2,301

ROSE PLANT

Luciano Moro, San Remo, Italy, assignor to Jackson & Perkins Company, Newark, N.Y., a corporation of New York Filed Oct. 4, 1962, Ser. No. 228,510
1 Claim. (Cl. Plt.—15)

The present invention relates to a new and distinct variety of rose plant of the hybrid tea class, which was originated by me by crossing the variety known as "Golden Rapture" (unpatented) with the variety known as "Golden Scepter" (U.S. Plant Patent No. 910).

The primary objective of this breeding was to produce a new and improved rose variety which is particularly suitable for greenhouse cut flower forcing. This objective was fully achieved, as evidenced by the following unique combination of characteristics which are outstanding in the new variety and which distinguish it from its parents, as well as from all other varieties of which I am aware:

(1) A leathery foliage texture;

(2) Stiff flower petals;

(3) A distinctive and attractive general color tonality of the flowers corresponding to Empire Yellow, lightly overcast with Pinard Yellow;

(4) Good flower color retention, with consequent unfading blooms, contrary to the blooms of the parent variety "Golden Rapture"; and (5) Suitability for greenhouse cut flower forcing.

Asexual reproduction of my new variety by budding, as performed at Newark, New York, U.S.A., and also at Pleasanton, California, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—"Golden Rapture."

*Pollen parent.*—"Golden Scepter."

Classification:

*Botanic.*—Hybrid tea.

*Commercial.*—Hybrid tea.

*Flower*

(Observations made from specimens grown in a greenhouse at Newark, New York, U.S.A., near mid-morning during the middle of the month of December.)

Blooming habit: Recurrent—continuous.

Bud:

*Size.*—Large.

*Form.*—Ovoid (is not affected by wet or hot weather).

*Color.*—When sepals first divide—Strontian Yellow, Plate 16. When petals begin to unfurl—Light Cadmium, Plate 4. When half-blown: inside of petals—Light Cadmium, Plate 4; reverse of petals—Apricot Yellow, Plate 4, with lower half of petals lightly overcast with Buff Yellow, Plate 4.

*Sepals.*—Slightly branched; curl back when petals begin to unfurl. Color: inside—Kildare Green, Plate 31; outside—Spinach Green, Plate 5.

*Calyx.*—Color—Spinach Green, Plate 5. Shape— apple. Size—small. Aspect—smooth. Odor when rubbed—none.

*Peduncle.* — Length — medium. Aspect — smooth. Strength — erect; heavy. Color — Oil Green, Plate 5.

*Opening.*—Opens up well; is not affected by adverse weather conditions.

Bloom:

*Size.*—Large. Average size when fully expanded—from 5 inches to 5½ inches.

*Borne.*—Singly.

*Stems.*—Medium length; strong.

*Form (when first open).*—Cupped. Permanence—retains its form to the end, but outer petals curl back.

*Petalage.*—Double (full but open center); stiff. Number of petals under normal conditions—from 40 to 45.

*Color.*—Center of flower—Apricot Yellow, Plate 4. Outer petals—Pinard Yellow, Plate 4. Base of petals (aiglet)—Lemon Yellow, Plate 4. Inside of petals—Empire Yellow, Plate 4, lightly overcast with Pinard Yellow, Plate 4. Reverse of petals—Baryta Yellow, Plate 4, lightly overcast with Pinard Yellow, Plate 4. General tonality from a distance—Empire Yellow, Plate 4, lightly overcast with Pinard Yellow, Plate 4.

*Discoloration.*—General tonality at end of first day—Empire Yellow, Plate 4, lightly overcast with Pinard Yellow, Plate 4. Second day—Empire Yellow, Plate 4, lightly overcast with Pinard Yellow, Plate 4. Third day—Pinard Yellow, Plate 4, very lightly overcast with Empire Yellow, Plate 4.

Petals:

*Texture.*—Thick; is not affected by wet or hot weather.

*Appearance.*—Inside—satiny. Outside—shiny.

*Form.*—Oval.

*Arrangement.* — Imbricated (regularly arranged shingle-like).

*Petaloids in center.*—Few; large.

*Persistence.*—Drop off cleanly.

*Fragrance.*—Moderate. Nature—tea (average hybrid tea scent).

*Lasting quality.*—On the plant—long. As cut flower—Very long.

*General Organs*

Stamens, anthers: Large; many; regularly arranged around styles. Color—Empire Yellow, Plate 4.

Stamens, filaments (threads): Long. Color—Pinard Yellow, Plate 4.

Pollen: Color—Baryta Yellow, Plate 4.

Styles: Bunched; uneven length; medium length; thin.

Stigmas: Color—Picric Yellow, Plate 4.

Ovaries: All enclosed in calyx.

Hips: None.

Seeds: None.

*Plant*

Form: Bush.

Growth: Vigorous; upright.

Foliage: Compound of 3–5 leaflets.

*Size.*—Large.

*Quantity.*—Normal.

*Color.*—New foliage: upper side—Grass Green, Plate 6, with outer edge lightly overcast with Garnet Brown, Plate 1; under side—Buffy Citrine, Plate 16. Old foliage: upper side—Dark Cress Green, Plate 31; under side—Light Bice Green, Plate 17.

*Shape.*—Oval pointed.

*Texture.*—Upper side—leathery. Under side—smooth.

*Ribs and veins.*—Ordinary.

*Edge.*—Serrated (saw-toothed).

*Serrations.*—Both double and single; small.

*Leaf stem.*—Color—Cerro Green, Plate 5. Under side—prickly.

*Stipules.*—Long; smooth.

Wood:

*New wood.*—Color—Yellowish Oil Green, Plate 5. Bark—smooth.

*Old wood.*—Color—Cress Green, Plate 31. Bark—smooth.

Thorns:

*Thorns.*—Quantity: on main stalks from base—many; on laterals from stalk—ordinary. Form—narrow base; medium length; hooked downward.

Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a leathery foliage texture, stiff flower petals, a distinctive and attractive general color tonality of the flowers corresponding to Empire Yellow, lightly overcast with Pinard Yellow, good flower color retention, with consequent substantially unfading blooms, and good suitability for greenhouse cut flower forcing.

No references cited.